US00PP17424P2

(12) United States Plant Patent
Bergman

(10) Patent No.: US PP17,424 P2
(45) Date of Patent: Feb. 20, 2007

(54) ***CHRYSANTHEMUM* PLANT NAMED 'YOKEY LARGO'**

(50) Latin Name: *Chrysanthemum×morifolium*
Varietal Denomination: Yokey Largo

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 29 days.

(21) Appl. No.: 11/157,457

(22) Filed: Jun. 21, 2005

(51) Int. Cl.
*A01H 5/00* (2006.01)

(52) U.S. Cl. ..... Plt./296
(58) Field of Classification Search ..... Plt./296
See application file for complete search history.

(56) References Cited

U.S. PATENT DOCUMENTS

PP11,756 P2 * 1/2001 VandenBerg ..... Plt./295

OTHER PUBLICATIONS

UPOV ROM GTITM Computer Database, GTI Jouve Retrieval Software 2006/05 Citation for 'Yokey Largo'.*

* cited by examiner

*Primary Examiner*—Wendy Haas
(74) *Attorney, Agent, or Firm*—C. A. Whealy

(57) ABSTRACT

A new and distinct cultivar of *Chrysanthemum* plant named 'Yokey Largo', characterized by its uniform and somewhat outwardly spreading plant habit; strong and freely branching growth habit; dark green-colored foliage; uniform flowering response and habit; can be grown as a spray-type or without bud removal; eary flowering habit; small anemone-type inflorescences with elongated oblong-shaped ray florets; bronze-colored ray florets and reddish purple-colored disc florets; and good postproduction longevity with plants maintaining good substance and color for about three to four weeks in an interior environment.

2 Drawing Sheets

Botanical designation: *Chrysanthemum×morifolium.*
Cultivar denomination: 'Yokey Largo'.

BACKGROUND OF THE INVENTION

The present Invention relates to a new and distinct cultivar of *Chrysanthemum* plant, botanically known as *Chrysanthemum×morifolium* and hereinafter referred to by the name 'Yokey Largo'.

The new *Chrysanthemum* is a product of a planned breeding program conducted by the Inventor in Salinas, Calif. and Alva, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made in February, 1999 in Salinas, Calif., of a proprietary selection of *Chrysanthemum×morifolium* identified as code number YB-6403, not patented, as the female, or seed, parent with a proprietary selection of *Chrysanthemum×morifolium* identified as code number YB-4447, not patented, as the male, or pollen, parent. The new *Chrysanthemum* was discovered and selected by the Inventor as a single flowering plant within the progeny of the stated cross-pollination grown in a controlled environment in Alva, Fla. in March, 2001. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Alva, Fla. in June, 2001. Asexual reproduction by cuttings has shown that the unique features of this new *Chrysanthemum* are stable and reproduced true to type in successive generations.

SUMMARY OF THE INVENTION

The cultivar Yokey Largo has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yokey Largo'. These characteristics in combination distinguish 'Yokey Largo' as a new and distinct *Chrysanthemum:*

1. Uniform, compact and somewhat outwardly spreading plant habit.
2. Strong and freely branching growth habit.
3. Dark green-colored foliage.
4. Uniform flowering response and habit.
5. Can be grown as a spray-type or without bud removal.
6. Early flowering, eight week response time.
7. Small anemone-type inflorescences with elongated oblong-shaped ray florets.
8. Bronze-colored ray florets and reddish purple-colored disc florets.
9. Good postproduction longevity with plants maintaining good substance and color for about three to four weeks in an interior environment.

Plants of the new *Chrysanthemum* can be compared to plants of the female parent selection. Plants of the new

*Chrysanthemum* differ from plants of the female parent selection primarily in ray floret color as plants of the female parent selection have light pink-colored ray florets. In addition, plants of the new *Chrysanthemum* are more outwardly spreading than plants of the female parent selection.

Plants of the new *Chrysanthemum* can be compared to plants of the male parent selection. Plants of the new *Chrysanthemum* differ from plants of the male parent selection primarily in ray floret color as plants of the male parent selection have yellow-colored ray florets.

Plants of the new *Chrysanthemum* can be compared to plants of the cultivar Yolafayette, disclosed in U.S. Plant Pat. No. 11,756. In side-by-side comparisons conducted in Alva, Fla., plants of the new *Chrysanthemum* differed from plants of the cultivar Yolafayette in the following characteristics:

1. Plants of the new *Chrysanthemum* and the cultivar Yolafayette differ in ray floret color as plants of the cultivar Yolafayette have yellow-colored ray florets.
2. Plants of the new *Chrysanthemum* and the cultivar Yolafayette differ in disc floret color as plants of the cultivar Yolafayette have golden yellow-colored disc florets.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yokey Largo' grown as spray-types.

The photograph on the second sheet comprises a close-up view of typical inflorescences of 'Yokey Largo' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted *Chrysanthemum* production. During the production of these plants, the following conditions were measured: day temperatures, 21° C. to 27° C.; night temperatures, 17° C. to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yokey Largo.

Commercial classification: Anemone-type potted *Chrysanthemum.*

Parentage:

*Female, or seed, parent.*—Proprietary selection of *Chrysanthemum×morifolium* identified as code number YB-6403, not patented.

*Male, or pollen, parent.*—Proprietary selection of *Chrysanthemum×morifolium* identified as code number YB-4447, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous anemone-type potted *Chrysanthemum* that can be grown as a spray-type or without bud removal. Upright with lateral branches somewhat outwardly spreading; uniformly mounded crown; compact growth habit. Strong and freely branching growth habit; about four lateral branches develop after removal of terminal apex (pinching); dense and full plants.

*Plant height.*—About 19 cm.

*Plant width.*—About 32 cm.

*Lateral branches.*—Length: About 16 cm. Diameter: About 4 mm. Internode length: About 1.2 cm. Strength: Strong. Texture: Pubescent. Color: 146A.

*Foliage description.*—Arrangement: Alternate; simple. Length: About 5.9 cm. Width: About 4.5 cm. Apex: Mucronate. Base: Truncate with attenuate tendencies. Margin: Palmately lobed, sinuses between lateral lobes parallel to divergent. Texture, upper and lower surfaces: Pubescent. Color: Developing and fully expanded foliage, upper surface: Close to 147A. Developing and fully expanded foliage, lower surface: More green than 147B. Venation, upper surface: Close to 147A to 147B. Venation, lower surface: Close to 147B. Petiole length: About 1.9 cm. Petiole diameter: About 3 mm. Petiole texture, upper and lower surfaces: Pubescent. Petiole color, upper surface: Close to 146A. Petiole color, lower surface: Close to 146A to 146B.

Inflorescence description:

*Appearance.*—Anemone-type inflorescence form with elongated oblong-shaped ray florets. Inflorescences borne on terminals above foliage. Disk and ray florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to two weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—Grown as a spray-type, about five per lateral branch.

*Inflorescence bud.*—Height: About 5 mm. Diameter: About 6.5 mm. Shape: Oblate. Color: Close to 146A.

*Inflorescence diameter.*—Small, about 4.3 cm.

*Inflorescence height.*—About 1.75 cm.

*Diameter of disc.*—About 3.3 cm.

*Receptacle diameter.*—About 5 mm.

*Receptacle height.*—About 5 mm.

*Ray florets.*—Length: About 2.1 cm. Width: About 5 mm. Corolla tube length: About 4 mm. Shape: Elongated oblong. Apex: Mostly acute. Base: Fused into a corolla tube. Margin: Entire. Orientation: Initially upright to eventually perpendicular to the peduncle. Texture, upper and lower surfaces: Smooth, glabrous; satiny. Number of ray florets per inflorescence: About 20 arranged in a single whorl. Color: When opening and fully opened, upper surface: Close to 6A overlain with close to 46A. When opening and fully opened, lower surface: Close to 6A underlain with close to 53A.

*Disc florets.*—Arrangement: Massed at center of receptacle. Length: About 1.75 cm. Diameter, apex: About 5 mm. Diameter, base: About 2.5 mm. Shape: Tubular; enlarged. Apex: Five-pointed. Number of disc florets per inflorescence: About 130. Color: Immature: Close to 187A. Mature, apex: Close to 9A overlain with 59A. Mature, mid-section: Close to 9A more faintly overlain with 59A. Mature, base: Close to 144A, towards the base, close to 155D.

*Phyllaries.*—Quantity per inflorescence: About 20 arranged in about two to three whorls. Length: About 6 mm. Width: About 3 mm. Shape: Lanceolate. Apex: Acute. Base: Truncate. Margin: Entire. Texture, upper surface: Waxy, smooth. Texture, lower surface: Pubescent. Color, upper surface: Close to 144A. Color, lower surface: Close to 146A.

*Peduncles.*—Length, terminal peduncle: About 3.7 cm. Length, fourth peduncle: About 5.4 cm. Diameter: About 2 mm. Strength: Strong. Texture: Pubescent. Angle: About 45° from vertical. Color: 144A to 146A.

*Reproductive organs.*—Androecium: Present on disc florets only. Anther length: Less than 1 mm. Anther color: Close to 12A. Pollen amount: None. Gynoecium: Present on both ray and disc florets. Style length: About 5 mm. Style color: Close to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yokey Largo', as illustrated and described.

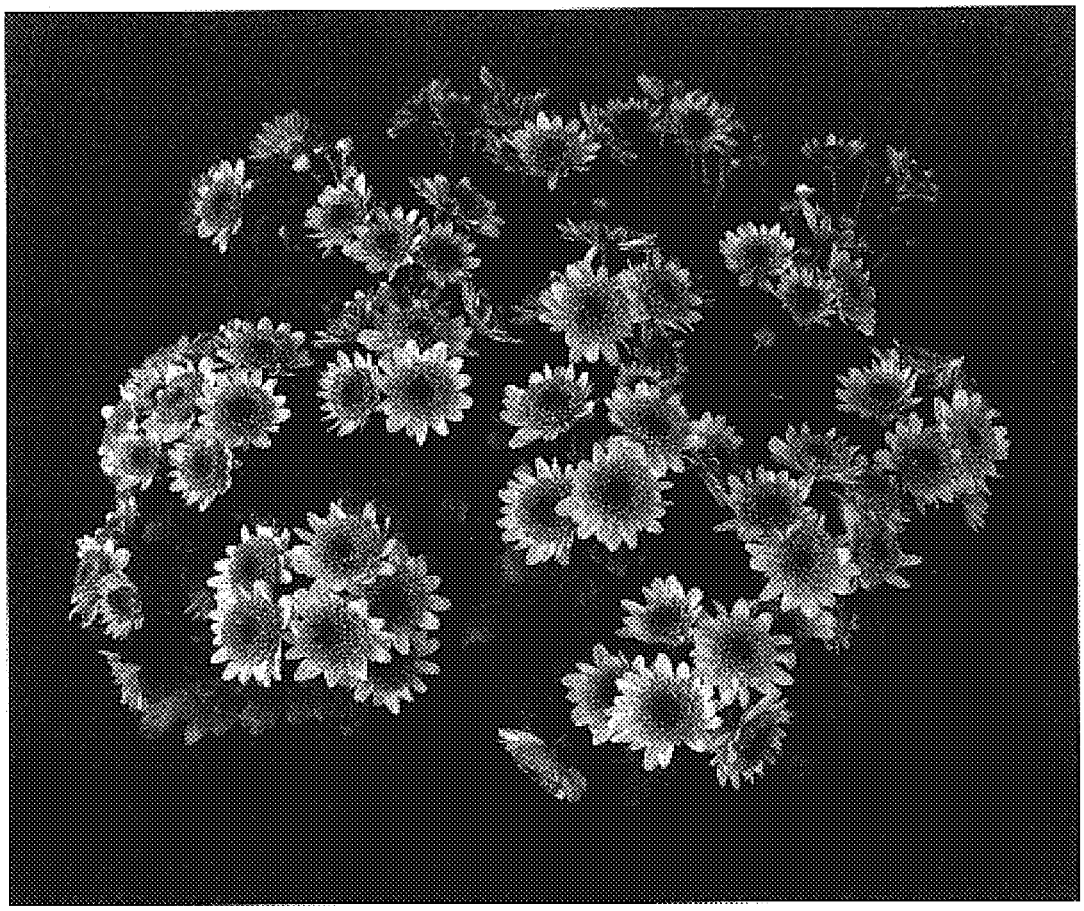

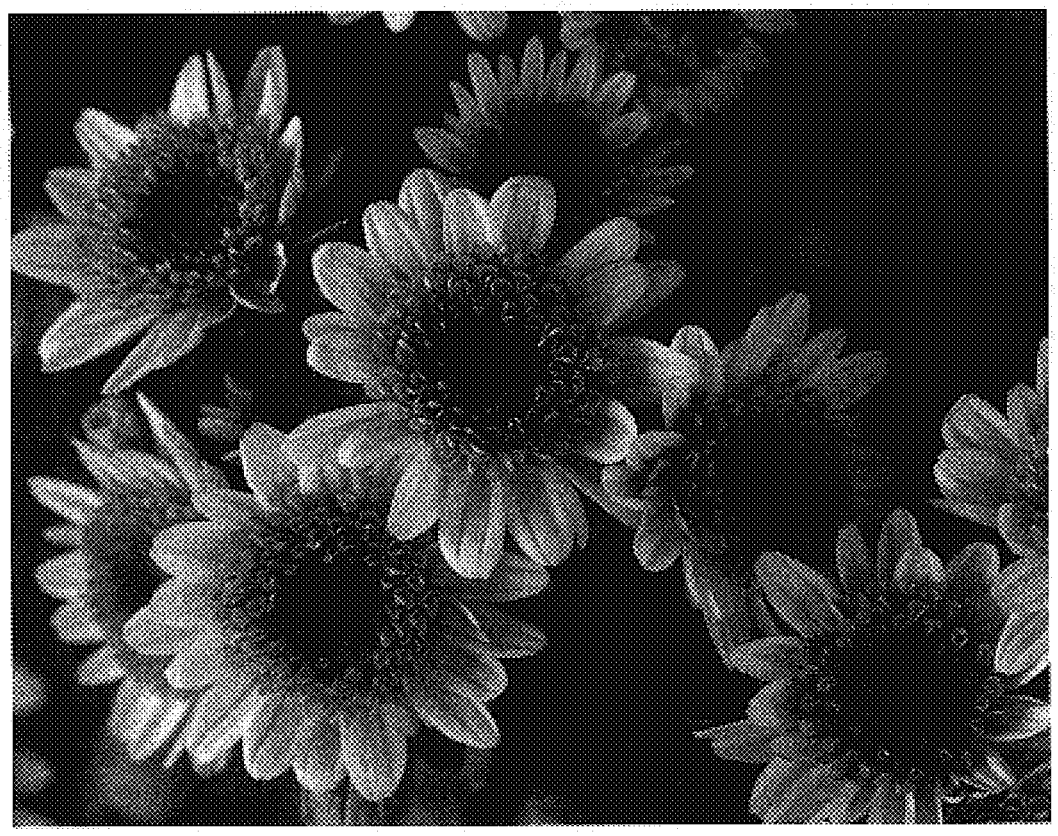

* * * * *